United States Patent [19]
Harrison

[11] 3,952,743
[45] Apr. 27, 1976

[54] SUCTION DEVICE

[75] Inventor: John Young Harrison, Sydney, Australia

[73] Assignee: Unisearch Limited, New South Wales, Australia

[22] Filed: Mar. 25, 1974

[21] Appl. No.: 454,765

[30] Foreign Application Priority Data
Mar. 28, 1973 Australia............................ 2780/73

[52] U.S. Cl. ............................................... 128/276
[51] Int. Cl.² .......................................... A61M 1/00
[58] Field of Search ........... 128/240, 276, 277, 278, 128/297, 302

[56] References Cited
UNITED STATES PATENTS

| | | | |
|---|---|---|---|
| 694,541 | 3/1902 | Gordon | 128/240 |
| 2,560,915 | 7/1951 | Bamberger | 128/350 R |
| 2,822,808 | 2/1958 | Boone | 128/276 |
| 3,406,967 | 10/1968 | Young | 272/8 N |
| 3,595,234 | 7/1971 | Jackson | 128/276 |

*Primary Examiner*—Channing L. Pace
*Attorney, Agent, or Firm*—Brisebois & Kruger

[57] ABSTRACT

A suction device for medical purposes which enables diseased tissue, such as brain tumor tissue, to be removed. No mechanical action is involved in the use of the suction device and therefore no blood vessels or healthy tissue is damaged.

2 Claims, 1 Drawing Figure

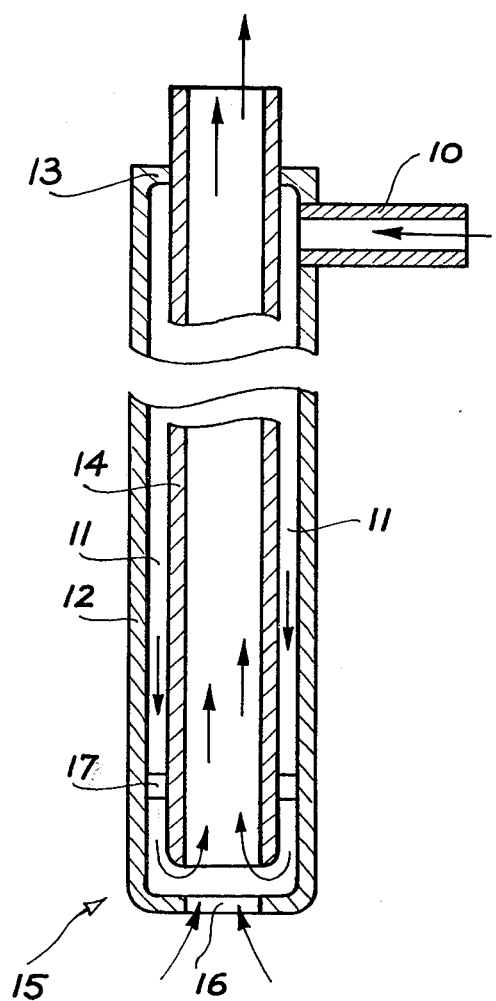

SUCTION DEVICE

BACKGROUND OF THE INVENTION

This invention relates to a suction device for medical purposes and particularly for the removal of brain tumors.

An object of the present invention is to provide a suction device for medical purposes which can be used to remove by suction unwanted areas of tissue. A further object is to provide such a device for use in the removal of brain tumors.

A device for the aforespecified purposes must be capable of being used with accuracy and must have a readily controllable and delicate action in view of the sensitive areas in which it may operate.

SUMMARY OF THE INVENTION

The device of the present invention is normally used with a low pressure of water (less than 5lb/in.$^2$) with an air suction system and is held and manipulated by the surgeon.

According to the present invention there is provided a suction device for medical purposes comprising inner and outer concentric tubes each having first and second ends wherein the first end of the outer tube is formed with an orifice for receiving unwanted tissue and the second end thereof comprises a wall through which the inner tube protrudes, the first end of the inner tube is located within the outer tube adjacent the orifice and the second end thereof is located externally of the outer tube and is arranged to be connected to a suction means and liquid inlet means is provided in the outer tube adjacent the wall such that, in use, liquid travels from the second to the first end of the outer tube to the region of the orifice and is then sucked up the inner tube by the suction means.

DESCRIPTION OF THE DRAWING

A preferred form of the present invention is described by way of example with reference to the accompanying drawing which is a sectioned side elevation.

DESCRIPTION OF THE REFERRED EMBODIMENTS

In operation a liquid such as water enters the device through a side entry pipe 10 into the space 11 between two concentric tubes 12, 14 the outer tube 12 having an end wall 13 at the upper end through which the inner tube 14 protrudes where it is connected to a suction device (not shown).

The water flows to the other or working end 15 of the outer tube 12 which is internally flanged to define an orifice 16 of lesser diameter than the bore of the outer tube and approximating in size to the bore of the inner tube 14 which terminates a short distance from the end of the outer tube.

The water as it reaches the end of the inner tube 14 is sucked up through it and discharged into the suction line taking with it any material which is swept away by the water as it passes the orifice.

Between the inner and outer tube and either separate from these or integral with them is a boss or swirl member(s) 17 which imparts a rotational movement to the water to give it a swirl effect to assist in removing any material at the orifice.

Optionally, an air bleed is provided to the inner tube of the device such that by placing a finger over the bleed hole suction intensity can be varied. The general suction effect and water head are designed so that there is no discharge of water at the orifice when the device is not in contact with any tissue.

The material as it is sucked up into the orifice and into the inner tube would normally tend to block it and reduce or destroy the suction effect however the swirl action breaks up the material so that it is swept away by the discharge water as small particles which because of the continuous flow do not adhere to the surfaces of the device.

As no mechanical action is involved no blood vessels or healthy tissue are damaged.

We claim:

1. A suction device for medical purposes comprising inner and outer concentric tubes, each having first and second ends, wherein the first end of said outer tube is formed with an orifice for receiving unwanted tissue and the second end thereof comprises a transverse end wall through which the inner tube protrudes, and the first end of the inner tube is located within the outer tube adjacent the orifice and the second end thereof is located externally of the outer tube and is adapted to be connected to suction means, liquid inlet means being provided in the outer tube adjacent said wall, and a swirl member being provided between said inner and outer tubes and between said inlet means and said orifice, said first end of said outer tube comprising a second transverse end wall a short distance beyond the first end of said inner tube and in which said orifice is located, said second wall limiting said orifice to an area in alignment with said inner tube and having a cross-section no greater than the cross-section of said inner tube, so that when suction means is applied to the second end of said inner tube liquid traveling from the second to the first end of the outer tube is given a swirling motion by said swirl member and then sucked into said inner tube without emerging from said first end of said outer tube.

2. A suction device as claimed in claim 1, which comprises means by which the suction intensity can be varied in use.

* * * * *